United States Patent [19]

Smith

[11] 4,069,177
[45] Jan. 17, 1978

[54] WATER ABSORBING AND URINE STABLE STEP-WISE GRAFTED STARCH-POLYACRYLONITRILE COPOLYMERS

[76] Inventor: Theodore Smith, 3305 Mulberry Avenue, Muscatine, Iowa 52761

[21] Appl. No.: 697,736

[22] Filed: June 21, 1976

[51] Int. Cl.² .............................................. C08L 3/02
[52] U.S. Cl. ..................... 260/17.4 GC; 47/DIG. 10; 128/284; 128/285; 128/290 R; 128/296; 260/17.4 ST
[58] Field of Search ................................ 260/17.4 GC

[56] References Cited

U.S. PATENT DOCUMENTS 3,997,484  12/1976  Weaver et al. ............... 260/174 GC

OTHER PUBLICATIONS

Chem. Absts. 66 (1967): 4050w; Fanta, "Graft Copolymers of Starch."

Primary Examiner—Edward M. Woodberry
Attorney, Agent, or Firm—Zarley, McKee, Thomte, Voorhees & Sease

[57] ABSTRACT

Alkali metal carboxylate salts of starch-polyacrylonitrile graft copolymers produced by saponifying a starch-polyacrylonitrile graft copolymer are improved significantly by employment of step-wise grafting of the acrylonitrile, and by employment of starch which has been treated by one or more of the following steps, thinning, defatting, precooking.

18 Claims, No Drawings

WATER ABSORBING AND URINE STABLE STEP-WISE GRAFTED STARCH-POLYACRYLONITRILE COPOLYMERS

BACKGROUND OF THE INVENTION

This invention relates to improved water insoluble alkali metal carboxylate salts of starch-acrylonitrile graft copolymers which are produced by saponifying starch acrylonitrile graft copolymers with a base in an aqueous alcoholic medium. The invention represents an improvement over my previous patent U.S. Pat. No. 3,661,815.

Graft copolymers of starch-polyacrylonitrile per se are known as well as are methods for their preparation.

Thus, it is known that acrylonitrile can be grafted on starch using ceric salts as catalysts to form starch-acrylonitrile graft copolymers. See, for example, U.S. Pat. No. 2,922,768. Such graft copolymers can also be prepared by the reaction of acrylonitrile with pre-irradiated starch which is prepared by irradiation of starch with gamma rays or an electron beam. See Reyes, Clark, Comas, Russell, and Rist, Nuclear Applications 6, 509–517 (1969). In such graft copolymers the starch serves as a backbone or building block on which the acrylonitrile is grafted and therefore the starch need be present in only very small proportions with respect to the polyacrylonitrile moiety.

After the starch polyacrylonitrile graft copolymer is produced to make it valuable as a water insoluble material having the ability to absorb large amounts of water, it is saponified. For example, U.S. Pat. No. 3,425,971 is directed to saponification of a graft copolymer in an aqueous potassium hydroxide solution.

Compositions which can readily absorb large amounts of water are valuable for many uses. For example, such substances can be used in manufacturing products such as disposable diapers, tampons, sanitary napkins, paper towels and in numerous hospital or nursing home applications such as bed sheets, application to gauzes or other wound dressing materials, or the like. In addition, such substances can be used in other areas of industry where water absorbing and retention is important. For example, it can be mixed with wood pulp or the like, or added to a soil in order to increase the water retention capability of the soil.

Ideally, water absorbing compositions should not only absorb as much water as possible and therefore be highly efficient in this respect, it must also not have the property of "thinning" after exposure to solutions that have a high salt and enzyme content. This is a very important consideration in that many of the body fluids which such a composition will come in contact with when used in disposable diapers, or sanitary napkins, have both a high salt content and a high enzyme content. Appreciable contact with both salts and enzymes will allow many water absorbing copolymers to become less viscous and even run with the water retention ability reduced after a short period of time. Thus, it is very important that not only the composition have high water absorbence capability, but it must also not be adversely affected so that it will thin upon contact with salt and enzyme containing liquids.

In addition, an ideal composition must be one which will have the ability to adhere to fibers of, for example, paper towels or other material upon which it is coated. Most graft copolymers, especially of starch polyacrylonitrile do not have a property of good adherence to a substrate material.

In addition, primarily for aesthetic purposes so that they will not interfere with the looks and quality of a product in which such water absorbing compositions are applied, a good polymer should provide a clear product when in dispersion form.

The object of this invention is to provide a starch polyacrylonitrile graft copolymer which has an unusually high water absorbence capacity, i.e., capable of absorbing from about 800 to as much as 1000 times its weight of water.

Another object of this invention is to provide a starch polyacrylonitrile graft copolymer which is capable of absorbing up to as much as 100 times or greater, of its weight of body fluids.

Still another object of this invention is to provide a starch polyacrylonitrile graft copolymer which has significantly improved characteristics in terms of improved performance in the presence of ionic and enzyme containing fluids in that the polymer paste does not thin upon standing.

A still further object of this invention is to provide a graft copolymer which, when in wet form, will form a paste like material which has good adhesion properties to a substrate material.

Yet another object of this invention is to provide a graft copolymer which has a high acrylonitrile content and yet which in a wet form dispersion is a clear product which will not interfere with the aesthetic characteristics of a substrate material to which it is applied.

The method and means of accomplishing at least all of the above stated objects will become apparent from the detailed description of the invention which follows.

SUMMARY OF THE INVENTION

This invention relates to an alkali metal carboxylate salt of a polyacrylonitrile graft copolymer produced by saponifying a starch polyacrylonitrile graft copolymer, with the copolymer being produced from starch by a step-wise grafting procedure. Starch is reacted with a portion of a predetermined amount of acrylonitrile in the presence of a free radical initiator to provide a partially grafted copolymer, and thereafter said partially grafted copolymer is reacted with the remaining portion of a predetermined amount of acrylonitrile in the presence of additional amounts of free radical initiator. Improved characteristics are also obtained wherein the starch, prior to copolymerization is treated starch which has been treated by one or more of the following procedures: Thinning, cooking and defatting.

DETAILED DESCRIPTION OF THE INVENTION

As heretofore briefly mentioned, it has been found that the water insoluble alkali metal carboxylate salts of starch acrylonitrile graft copolymers which are produced by saponifying starch acrylonitrile graft copolymers with a base in an aqueous alcoholic medium are significantly improved with respect to all the properties heretofore mentioned, wherein the grafting procedure is a step-wise grafting procedure. Step-wise grafting will be explained in more detail below with reference to the examples. The term, however, as will be apparent from the examples below, is utilized to mean adding a portion of the predetermined amount of acrylonitrile to the starch material and reacting them together to polymerize in the presence of a free radical initiator, such as ceric nitrate or ceric ammonium nitrate, and allowing the reaction to go until it has reached equilibrium conditions, i.e., the temperature has stabilized without any further exothermic reaction as evidenced by an increase in temperature, and thereafter adding the remaining portion of the acrylonitrile along with additional amounts of free radical initiator and allowing the reaction to again react until completion of the reaction as evidenced by constancy of the reaction temperature. Thereafter, preferably a hold time is employed in order to insure complete reaction.

As also heretofore mentioned, the product is improved even further if the starch which is employed is first treated by thinning, and/or defatting, and/or precooking. However, an improved product is obtained even if the starch is not thinned. cooked or defatted as long as step-wise grafting is employed. Thus, the starting starch can be the readily commercially available pearl starch which has not been thinned, cooked or defatted. Thinned starches are generally made by acid thinning, so that the cooked starch paste has a reduced viscosity; such starches are available in a wide viscosity range. A defatted starch is a pearl starch that has been treated to reduce fat content from 0.5% to about 0.1%. Precooking as the term is utilized herein, refers to the addition of water to the starch material and heating it up to a temperature near boiling in order to paste the starch.

It is not known why thinning, precooking or defatting, or for that matter step-wise grafting, improves the product. While applicant does not wish to be bound by any theory, it is believed that the thinning of the starch is an important factor, in that it allows viscosity control of the starch during any precooking which might occur and during the subsequent grafting step. It is believed that precooking of the starch, as described hereinbefore and as further described in the examples hereinafter allows grafting of the acrylonitrile into the whole starch mass rather than just grafting onto the periphery of the starch granule. In addition, there is a different type of grafting that occurs rather than when granular non-cooked starch is utilized as described in my previous patent, 3,661,815, in that utilization of a cooked starch allows more free radical sites for initiation of the grafting procedure. Step-wise grafting, it is believed, overcomes the undesired effects of the exothermic reaction wherein grafting with a high ratio of acrylonitrile occurs, as well as aids in keeping the water volume down to a workable level for the final saponification step. High temperatures should be avoided during grafting in that it reduces the functionality of the product and by utilization of the step-wise grafting, this is controlled.

As will be apparent from the examples below, step-wise grafting can be employed utilizing two or more steps. For example, three-step grafting is satisfactory. However, of course, economics enters into the overall processing picture and generally two steps are satisfactory to obtain maximum benefit from step-wise grafting without significantly increasing the economics of the process.

As heretofore mentioned, the saponificatin of starch polyacrylonitrile copolymers is known. Therefore, it will not be necessary to provide a detailed description of saponification. The portion of my previous patent, 3,661,815, describing saponification in an aqueous alcoholic medium is incorporated herein by reference. However, certain modifications in the saponification procedure have been found to be advantageous for the present process. Saponification can occur by reflux saponification in an unsealed vessel or pressurized saponification in a sealed vessel. Suitable saponification conditions for the practice of this invention are as follows:

| SAPONIFICATION CONDITIONS | | |
|---|---|---|
| | Practical Range | Preferred Range |
| Temperature | | |
| closed vessel | 90–98° C. | 90–95° C. |
| Open Vessel | (reflux conditions) | 76–80° C. (reflux conditions) |
| Time: Closed vessel | 1–2 hours | 90 minutes |
| open vessel | 4–6 hours | 4 hours |
| Grams of sodium hydroxide per 100 ml. aqueous alcoholic saponifying solution | 3.5–5.0 | 4.0 |
| Volume (ml) of saponifying solution per gram of starch acrylonitrile copolymers | 14–15 | 15 |
| % of water in alcoholic saponifying solution | 45–65 | 55 |

The conditions for the step-wise grafting procedure will be readily apparent from the many examples given below. However, as a guideline, the presently best known conditions for grafting starch with acrylonitrile by a two or three step grafting procedure are as follows:

| STEP-WISE GRAFTING CONDITIONS | | |
|---|---|---|
| Grafting Time | Time | |
| (2) step (a) 1st step | 30 minutes | |
| (b) 2nd step | 2 hours | |
| (3) step (a) 1st step | 30 minutes | |
| (b) 2nd step | 30 minutes | |
| (c) 3rd step | 2 hours | |
| Grafting Temperature | Practical Range | Optimum |
| (2) step (a) 1st step | 58–62° C. | 60° C |
| (b) 2nd Step | 58–62° C. | 60° C |
| Starch: Acrylonitrile Mole Ratio | 1:6 to 1:12 | 1:9 to 1:12 best 1:9 |
| Starches Defatted: | | |
| (a) Thinned viscosity | 65–80 Buel | 75–80 |
| (b) Cook | | 10 min. at 92–95° C. |
| (c) % fat | | 0.05–0.12% |
| Pearl: | | |
| (a) Thinned, viscosity | 65–80 Buel | 75–80 Buel |
| (b) Cooked | | 10 min. at 92–95° C. |

With regard to the table showing the saponification conditions, for convenience of description hereinafter, the volume in milliliters of saponifying solution per gram of starch acrylonitrile polymer will hereinafter be abbreviated as "Factor". With regard to the table on the grafting procedure, it can be seen that in the second and subsequent grafts, best results are obtained wherein the temperature does not rise above 62° C. Preferably the temperature is within the range from 58° to 62° C with the most preferred temperature being 60° C. The grafting time for the step-wise grafting procedure specified herein are generally minimum times which are desirable to use considering the economics of the process. Longer times could be employed however, the economics are insufficient to make them usable when considering the little additional grafting which will occur. The preferred starch acrylonitrile mole ratio range is from 1:9 and 1:12 with the best results being at 1:9. It has been found that the 1:9 ratio starch to acrylonitrile copolymer is the most resistant to enzymatic attach when in contact with body fluids containing enzymes.

As heretofore mentioned, a product of this invention has surprisingly high fluid absorption characteristics. In the grafting process, it has been found that the product made by grafting starch with acrylonitrile can be isolated and then grafted again with additional amounts of acrylonitrile in a step-wise grafting procedure employing two, three or more steps. This procedure of step-wise grafting permits the making of products with a starch acrylonitrile molar ratio as high as 1:12. This is normally not possible with a one-step grafting procedure since the grafting of starch with acrylonitrile gives a high exothermic reaction, with the increased temperature destroying the functionality of the polymer. In addition to make a product with a starch acrylonitrile molar ratio as high as 1:12 in one step would require excessive amounts of water in the reaction mixture in order to absorb the heat of reaction. In contrast, in step-wise grafting the amount of water needed is considerably reduced. The graft copolymer can be isolated and then saponified later in an aqueous methanolic sodium hydroxide solution in accord with the manner previously mentioned herein. Alternatively, the copolymer slurry resulting from step-wise grafting procedure can be saponified by adding additional water methanol and sodium hydroxide, immediately.

The following examples are offered to further illustrate but not limit the invention.

EXAMPLE 1

Starch Acrylonitrile Graft Polymer by Two-Step Grafting Procedure Utilizing Pearl Starch A slurry of 24.3 grams of granular pearl starch (0.15 mole on a dry solids basis) in 200 milliliter of water was cooled to 20° C. Acrylonitrile (35.2 grams, starch to Acrylonitrile mole ratio of 1:4.5), and 13.5 milliliter of ceric nitrate M/10 ceric ion in N/1 nitric acid were added in order that grafting would occur. A temperature rise to 58° C. occurred in ten minutes and thereafter the temperature of the mass was maintained at 60° C. for a total grafting time of 30 minutes. The slurry was cooled to 30° C. and the copolymer was grafted a second time by adding 100 milliliter of water, 35.8 grams of acrylonitrile to provide again a starch to acrylonitrile mole ratio of 1:9 and 18 milliliter of ceric nitrate solution was added. After the reaction exothermed (to 51° C. in 36 minutes) the slurry was heated to 60° C. for a total grafting time of 2 hours. The copolymer product was washed and dried. In similar manner, starch to acrylonitrile graft copolymers with starch to acrylonitrile mole ratio of 1:9 and 1:12 were made up using a three step grafting procedure by grafting 1:3 and 1:4 starch to acrylonitrile mole ratios per grafting step, respectively.

EXAMPLE 2(a) Preparation of Starch Acrylonitrile Graft Copolymers Using Cooked Acid Thinned Pearl Starch and Defatted Thinned Starches by a Two-Step Grafting Procedure.

Pearl starch was defatted by continuous extraction of the starch with 85% methanol and 15% water solution, at reflux temperatures. The starch was thinned with hydrochloric acid during the extraction of the fat. The percent fat was 0.05% and the viscosity was 65 Buel. The defatted thinned corn starch (24.0 grams) was slurried in 250 milliliters of water. This slurry was heated in a glass flask by a hot water bath to temperatures within the range of 92° C to 95° C and held at that temperature for 10 minutes. The starch was now a cooked starch and was thereafter cooled to 20° C and 100 milliliters of water and 35.8 grams of acrylonitrile as well as 15 milliliters of ceric nitrate free radical initiator were added in that order. After the reaction temperature leveled off at 55° C the slurry was heated to 60° C and maintained there for a total grafting time of 30 minutes. The mass was cooled to 30° C and the second step of a step-wise grafting procedure was carried out by adding to the slurry, 75 milliliters of water, 35.8 grams of acrylonitrile and 18 milliliters of ceric nitrate free radical initiator, in the order mentioned herein. After the reaction exothermed and leveled off at 55° C., the reaction mixture was heated to 60° C. and maintained there for 2 hours to allow the second portion of the step-wise grafting to occur.

Thereafter, the completely grafted product was used directly in a final saponification step by adding water, methanol and sodium hydroxide in a manner previously disclosed herein in the table labeled "Saponifying Conditions".

The thinning of the starch gave a lower viscosity which was found desirable in both the cooking step and the grafting step. Unthinned starch has a tendency to provide a difficultly workable high viscosity during cooking and especially in the starch grafting steps. A satisfactory viscosity range has been found to be 65 to 80 Buel. The Buel viscosity was determined by slurring 4.5 grams, on a dry solids basis, of starch in 10 milliliter of water and thereafter adding 90 milliliter of a 1% sodium hydroxide solution to the slurry with stirring for three minutes. The beaker containing the slurry was then put in a water bath at 25° C. for 30 minutes and the paste was poured into a Buel funnel fitted with an orifice. The milliliter of paste collecting in 70 seconds is termed the Buel viscosity.

EXAMPLE 3(A), 3(B) and 3(C). Showing Saponification of a Starch Acrylonitrile Graft Copolymers by Pressure Saponification and Reflux Saponification.

A. Isolated Dried Starch Graft Copolymer, 12 grams, was added to a 7 ounce pressure vessel containing 180 milliliters of a mixture made of 7.2 grams of sodium hydroxide and 96.4 milliliters of water and 79.9 milliliters of anhydrous methanol. The vessel was sealed and placed in a water bath at 75° C. The water bath was heated to 95° C. and the vessel was shaken several times to prevent the settling of the product until the contents had thickened adequately. The heating was continued for 90 minutes and then the reaction container was removed and cooled. The saponified product was removed from the vessel and blended to a uniform paste in a blender. Purification of the saponified product by removal of the water, ammonia, excess sodium hydroxide and any soluble salts resulting from the neutralization was accomplished by a series of a product treatment with anhydrous methanol. The final product was neutralized within the PH range of 6.0 to 8.0 with glacial acetic acid, was filtered and dried at 60° C. in a vacuum oven.

The volume of the saponifying liquid was determined by a numerical factor, previously mentioned hereinbefore. That factor was 12 (grams on a dry basis solids of graft copolymer times the numerical factor) 15 to provide the volume of saponifying liquid here 180 milliliter.

B. Non-isolated graft copolymer was saponified in a closed vessel at a pressure within the range of 25 to 30 pounds per square inch as follows: 47.6 grams of slurry (25.22% solids, 12 grams of solids) was mixed with 14.4 grams of a 50% sodium hydroxide solution, 55.8 milliliters of water and 81 milliliters of methanol in a 7 ounce pressure vessel. This mixture had the same composition as described under example 3(a). It was treated and purified as shown in Example 3(a).

C. Graft copolymer slurry saponification by reflux conditions.

The entire batch of graft copolymer (278 grams of slurry, 47.9 grams of solids) were mixed with 57.4 grams of 50% sodium hydroxide, 150 milliliters of water and 305 milliliters of methanol in a one liter, three necked flask fitted with a stirrer thermometer and a reflux condenser. The flask was heated in a hot water bath at a reflux temperature within the range of 77° to 79° C. for a period of four hours. The saponified mixture was cooled and the product was purified with anhydrous methanol. The composition of the liquid of the saponification phase was 4.0% sodium hydroxide, 55% water and 45% methanol.

EXAMPLES 4–6

In these examples a granular pearl starch was grafted with acrylonitrile in a three step step-wise grafting procedure. The grafting procedure was exactly the same as that provided in Example 1. The starch to acrylonitrile mole ratio for each grafting step was 1:3 to provide a total molar ratio of starch to acrylonitrile of 1:9. The samples of the slurry were withdrawn at each step and saponified. Saponification of the examples 4, 5, and 6 were in accord with the following table:

TABLE 1a

|  | Grams of Solids (Product) | Factor | % Sodium Hydroxide | % Water | Saponification Type, Example |
|---|---|---|---|---|---|
| Example 4 | 15 | 13.3 | 4.0 | 50 | 3B |
| Example 5 | 15 | 13.3 | 4.5 | 50 | 3B |
| Example 6 | 15 | 13.3 | 5.0 | 50 | 3B |

The following table summarizes the grafting conditions for examples 4, 5 and 6 and shows the liquid uptake of the resulting polymer using water and a 0.4% sodium chloride solution. A 0.4% sodium chloride solution approximates the liquid uptake for human urine.

TABLE 1b

|  | Grafting Step | Starch:An (acrylonitrile) Molar Ratio | Liquid Uptake ml/g of Product | |
|---|---|---|---|---|
|  |  |  | Water | 0.4% Sodium Chloride |
| Example 4 | 1 | 1:3 | 110 | 64 |
| Example 5 | 2 | 1:6 | 180 | 76 |
| Example 6 | 3 | 1:9 | 270 | 96 |

EXAMPLES 7–9

In these examples, granular defatted pearl starch (0.08% fat) was grafted in the same manner as in Examples 4–6. Samples of the slurry were removed at each step-wise grafting step and saponification under the conditions specified below occurred:

TABLE 2

GRAFTING AND SAPONIFICATION CONDITIONS FOR EXAMPLES 7–9

| Ex. | Grafting Steps | Starch:AN Molar Ratio | Grams | Factor | % Sodium Hydroxide | % Water | Saponification type, example | yield grams | Liquid Uptake Water | 4% Sodium Chloride |
|---|---|---|---|---|---|---|---|---|---|---|
| 7 | 1 | 1:3 | 15 | 13.3 | 4.0 | 50 | 3B | 22 | 131 | 56 |
| 8 | 2 | 1:6 | 15 | 13.3 | 4.5 | 50 | 3B | 23 | 202 | 72 |
| 9 | 3 | 1:9 | 15 | 13.3 | 5.0 | 50 | 3B | 24 | 350 | 86 |

EXAMPLES 10–11

Employed in these examples was a defatted, thinned granular pearl starch which was grafted with acrylonitrile by a three-step grafting procedure, as defined in Example 1. The product was isolated, washed, dried and saponified. The starch acrylonitrile molar ratio, the grams of product employed, the factor as previously defined herein, and the saponification conditions as well as the liquid uptake for both water and a 0.4% sodium chloride solution for this product, are shown in Table 3 below.

TABLE 3

| Ex. | Starch:AN Molar Ratio | Grams | Factor | % Sodium Hydroxide | % Water | Saponification type | gram product | Liquid Uptake ml/gr product Water | 0.4% Sodium Chloride |
|---|---|---|---|---|---|---|---|---|---|
| 10 | 1:9[1] | 15 | 13.3 | 4.5 | 55 | 3C | 21.9 | 310 | 100 |
| 11 | 1:9[1] | 15 | 13.3 | 4.5 | 55 | 3C | 23.0 | 325 | 86 |

The percent fat for the defatted starch was 0.05% and the Buel viscosity was 65.

EXAMPLE 12

In this example, granular pearl starch was grafted by a three step grafting procedure as shown in Example 1. The final product after the three step grafting procedure was isolated, washed and dried. Again, the starch to acrylonitrile mole ratio, the conditions of saponification of the polymer, and the liquid uptake of the final product are shown in Table 4.

TABLE 4

| Ex. | Starch:AN Molar Ratio | Grams | Factor | % Sodium Hydroxide | % Water | Saponification Type | Grams Product | % N$_2$ | Liquid Uptake Ml/g of product: Water | 0.4% Sodium Chloride |
|---|---|---|---|---|---|---|---|---|---|---|
| 12 | 1:9 | 15 | 13.3 | 4.5 | 50 | 3C | 22.0 | 5.1 | 309 | 84 |

EXAMPLES 13-18

In these examples, a granular thinned defatted starch was grafted by the three step grafting procedure previously specified herein in Example 1, at a 1:3 starch to acrylonitrile molar ratio per step. Saponification conditions were varied in that an increase in the factor from 13.3 to 14 and 15 was employed and an increase in water of from 50% to 55% during saponification was employed. This was found to improve the product somewhat in terms of its liquid uptake. Table 5 summarizes the data for these examples.

TABLE 5

| Ex. | Starch:AN Molar Ratio | Grams | Factor | % Sodium Hydroxide | % Water | Saponification Type | Grams Product | Liquid Uptake ml/g of product: % $N_2$ | Water | 0.4% Sodium Chloride |
|---|---|---|---|---|---|---|---|---|---|---|
| 13 | 1:9[1] | 12 | 13.3 | 3.5 | 50 | 3A | 17.7 | 5.05 | 262 | 75 |
| 14 |  | 12 | 13.3 | 4.0 | 50 | 3A | 18.2 | 5.6 | 275 | 89 |
| 15 |  | 12 | 13.3 | 4.5 | 50 | 3A | 18.2 | 5.0 | 250 | 84 |
| 16 |  | 12 | 14 | 4.0 | 50 | 3A | — | 5.0 | 270 | 84 |
| 17 |  | 12 | 14 | 4.0 | 55 | 3A | — | 5.1 | 380 | 97 |
| 18 |  | 12 | 15 | 4.0 | 55 | 3A | — | 5.2 | 400 | 97 |

[1]Defatted starch (0.09%), thinned (Buel 72), and preswelled at 60° C. for ½ hour.

EXAMPLES 19-35

A graft copolymer which was made by two and three-step grafting procedures. Starch employed was a granular defatted, thinned and granular pearl starch. In examples 19, 20, 21, 22 and 23, the starches were pre-swelled at 60° C. In examples 24 and 25, the starches were not pre-swelled. Pre-swelling of the starch did not seem to improve the final product. From the data summarized in table 6 below, it appears that the use of a 55% water solution during saponification increased the liquid uptake of the final product. The use of defatted starches gaves a somewhat improved final product over the use of non-defatted pearl starch.

No thinning of the urine tested product of examples 19 and 20 occurred after 24 hours showing that the product seemed to exemplify a resistance to enzyme attack.

EXAMPLES 26-29

In these examples granular defatted thinned starch with variable fat contents were used in a two-step grafting procedure. The data is summarized in Table 7 below. The data shows that a fat content in the range of from 0.5% to 0.12% seems to have no marked effect on the final product.

TABLE 7

| Ex. | % fat | % $N_2$ | Starch:An Molar Ratio | Grams | Factor | % Sodium Hydrox. | % Water | Saponification Type | Grams Product | Liquid Uptake ml/g of Product % $N_2$ | $H_2O$ | 0.4% Sodium Chloride |
|---|---|---|---|---|---|---|---|---|---|---|---|---|
| 26 | 0.05 | 19.1 | 1:9 | 12 | 15 | 4.0 | 55 | 3A | 19.6 | 5.1 | 444 | 104 |
| 27 | 0.09 | 19.2 | 1:9 | 12 | 15 | 4.0 | 55 | 3A | 19.1 | 5.2 | 480 | 110 |
| 28 | 0.12 | 18.9 | 1:9 | 12 | 15 | 4.0 | 55 | 3A | 19.4 | 5.2 | 362 | 97 |

EXAMPLES 29-36

For these examples grafting was accomplished by a two-step grafting procedure employing a starch which had been cooked in accordance with Example 2 prior to grafting. The starches were defatted, thinned and a thinned pearl starch. As can be seen from Table 8 below which summarizes the data for these examples, the use of a cooked starch for grafting rather than a granular starch produces a saponified polymer which has a marked increase in liquid uptake. Moreover, there was no thinning of urine tested product paste in a 24 hour period showing good resistance to enzyme attack. Similarly, polymers made with cooked starch and grafted with low mole ratios of starch to acrylonitrile, i.e., about 1:3 thinned, when tested with urine.

TABLE 6

| Ex. | Starch % fat | thinned | pre-swelled | graft steps | Starch:AN Molar Ratio | grams | factor | % Sodium Hydrox. | % Water | Saponification type | Grams Product | Liquid Uptake ml/g of product: % $N_2$ | $H_2O$ | 0.4% Nacl | Urine |
|---|---|---|---|---|---|---|---|---|---|---|---|---|---|---|---|
| 19 | 0.09 | + | + | 2 | 1:9 | 12 | 15 | 4.0 | 55 | 3A | 18.3 | 5.0 | 500 | 110 | 100 |
| 20 | 0.09 | + | + | 2 | 1:9 | 12 | 15 | 4.0 | 50 | 3A | 18.5 | 4.9 | 360 | 100 | 100 |
| 21 | 0.09 | + | + | 3 | 1:12 | 12 | 15 | 4.0 | 55 | 3A | 18.4 | 5.1 | 530 | 110 |  |
| 22 | 0.09 | + | + | 3 | 1:12 | 12 | 15 | 4.0 | 50 | 3A | 18.0 | 5.1 | 412 | 100 |  |
| 23 | 0.5 | — | + | 2 | 1:9 | 12 | 15 | 4.0 | 55 | 3A | 19.5 | 5.3 | 330 | 94 |  |
| 24 | 0.5 | — | — | 2 | 1:9 | 12 | 15 | 4.0 | 55 | 3A | 19.1 | 5.6 | 378 | 96 |  |
| 25 | 0.09 | + | — | 2 | 1:9 | 12 | 15 | 4.0 | 55 | 3A | 19.1 | 5.2 | 480 | 110 |  |

TABLE 8

| Ex. | Viscosity Buel | % fat | Starch:AN Molar Ratio | Grams | Factor | % Sodium Hydrox. | % Water | Saponification type | Grams Product | Liquid Uptake ml/g of Product % $N_2$ | $H_2O$ | 0.4% Nacl | Urine |
|---|---|---|---|---|---|---|---|---|---|---|---|---|---|
| 29 | 72 | 0.09 | 1:9 | 12 | 15 | 4.0 | 55 | 3B | 19.6 | — | 1000 | 140 | 130 |
| 30 | 79.5 | 0.5 | 1:9 | 24 | 15 | 4.0 | 55 | 3B | 39.2 | — | 900 | 126 | 114 |
| 31 | 65 | 0.05 | 1:9 | 12 | 15 | 4.0 | 55 | 3B | 17.4 | 5.4 | 936 | 117 | 117 |
| 32 | 65 | 0.05 | 1:9 | 12 | 15 | 4.0 | 60 | 3B | 17.1 | 5.4 | 1000 | 117 | 118 |

TABLE 8-continued

| Ex. | Viscosity Buel | % fat | Starch:AN Molar Ratio | Grams | Factor | % Sodium Hydrox. | % Water | Saponification type | Grams Product | Liquid Uptake ml/g of Product | | |
|---|---|---|---|---|---|---|---|---|---|---|---|---|
| | | | | | | | | | | % N₂ | H₂O | 0.4% Nacl | Urine |
| 33 | 72 | 0.09 | 1:9 | 12 | 15 | 4.0 | 55 | 3B | 17.1 | 5.2 | 900 | 124 | 121 |
| 34 | 72 | 0.09 | 1:9 | 12 | 15 | 4.0 | 60 | 3B | 16.7 | 5.0 | 968 | 133 | 121 |
| 35 | 74 | 0.12 | 1:9 | 12 | 15 | 4.0 | 55 | 3A | 17.5 | 5.3 | 920 | 117 | 115 |
| 36 | 74 | 0.12 | 1:9 | 12 | 15 | 4.0 | 65 | 3A | 18.0 | 5.4 | 940 | 118 | 110 |

The conductance for 0.4% sodium chloride solution was 7200 micromhos, for urine the conductance is 5360 micromhos. This shows that 0.4% sodium chloride solution will behave similar to urine.

EXAMPLES 37–44

In these examples a series of three different thinned cooked pearl starches were grafted with acrylonitrile by a two-step procedure, as in example 2 and the product was thereafter saponified. Cooked, thinned pearl starch, as seen in Table 9, produces a final product with improved liquid uptake over granular starch products. Generally defatted starch products give somewhat improved liquid uptake over thinned pearl products. Variation in water volume during saponification seemed to have a significant effect on water uptake, but only a slight improvement in uptake of a 0.4% sodium chloride solution as well as body fluid uptake. Data from Table 8 and Table 9 below shows that the best products were made using defatted or pearl, thinned, cooked starch grafted by a two-step procedure to a starch acrylonitrile mole ratio of 1:9 and saponified in a solution containing 4.0% sodium hydroxide, 55% water, and 45% methanol.

TABLE 9

| Ex. | Viscosity Buel | Starch:AN Molar Ratio | Grams | Factor | % Sodium Hydrox. | % Water | Saponification Type | Grams Product | % nitrogen (Kjehldahl) Procedure | Liquid Uptake ml/g of product | | |
|---|---|---|---|---|---|---|---|---|---|---|---|---|
| | | | | | | | | | | Water | 0.4% Sodium Chloride | Urine |
| 37 | 79.5 | 1:9 | 12 | 15 | 4.0 | 45 | 3B | 17.3 | 5.1 | 628 | 105 | 111 |
| 38 | 79.5 | 1:9 | 12 | 15 | 4.0 | 50 | 3B | 17.1 | 5.1 | 690 | 107 | 117 |
| 39 | 79.5 | 1:9 | 12 | 15 | 4.0 | 55 | 3B | 16.9 | 5.4 | 900 | 115 | 116 |
| 40 | 79.5 | 1:9 | 12 | 15 | 4.0 | 60 | 3B | 16.7 | 5.1 | 920 | 116 | 114 |
| 41 | 79.5 | 1:9 | (47.8) | 15 | 4.0 | 55 | 3C | 76.0 | 5.1 | 840 | 119 | 119 |
| 42 | 79.5 | 1:12 | (59) | 15 | 4.0 | 55 | 3C | 84.8 | 5.6 | 1000 | 120 | 110 |
| 43 | 73 | 1:9 | (47.8) | 15 | 4.0 | 55 | 3C | 68.0 | — | 840 | 105 | — |
| 44 | 80 | 1:9 | (47.8) | 15 | 4.0 | 55 | 3C | — | — | 840 | 110 | 110 |

No reduction of viscosity of the urine tested product occurred in a 24 hour period.

As can be seen from the above identified examples, the employment of step-wise grafting procedure, in combination with one or more of the use of a thinned starch, a cooked starch, or a defatted starch, provides a product having significant advantages. The product where step-wise grafting and thinned, cooked pearl or defatted starches are used has resistance to enzyme activity, will not become less viscous when subjected to urine for a 24 hour period, has the ability to absorb more than 100 times its weight in body fluid, the ability to absorb between 800 and 1000 times its weight of water, when in a paste form will adhere to a substrate material, is clear, and in general represents a significantly improved starch polyacrylonitrile polymer composition. While only ceric free radical initiators have been employed in these examples, it is well understood by those skilled in the art that other free radical initiators might also be employed.

As can be seen, the invention accomplishes all of the stated objects, and represents a significant improvement in the art.

What is claimed is:

1. An alkali metal carboxylate salt of a starch-polyacrylonitrile graft copolymer produced by saponifying a starch polyacrylonitrile graft copolymer, said copolymer being produced by step-wise grafting of starch by acrylonitrile, the mole ratio of said starch to acrylonitrile being at least 1:6.

2. The product of claim 1 wherein said starch is a defatted starch.

3. The product of claim 1 wherein said starch is a cooked starch.

4. The product of claim 2 wherein said starch is a cooked starch.

5. The product of claim 1 wherein said step-wise grafting is a two-step grafting procedure.

6. The product of claim 1 wherein said step-wise grafting is a three-step grafting.

7. An alkali metal carboxylate salt of a starch polyacrylonitrile graft copolymer said salt being produced by saponifying a starch-polyacrylonitrile graft copolymer, said copolymer having a starch to acrylonitrile mole ratio of at least 1:6 and being produced from a thinned starch by step-wise grafting.

8. The product of claim 7 wherein said starch acrylonitrile mole ratio is within the range of about from 1:9 to about 1:12.

9. The product of claim 8 wherein said starch is a cooked starch.

10. The product of claim 8 wherein said starch is a defatted starch.

11. A process of preparing a starch polyacrylonitrile graft copolymer, said process comprising:
reacting starch with a portion of a predetermined amount of acrylonitrile, in the presence of a free radical initiator to provide a grafted copolymer, and thereafter, reacting said grafted copolymer with the remaining portion of said predetermined amount of acrylonitrile in the presence of additional amounts of free radical initiator to provide a more highly grafted copolymer, the mole ratio of said starch to acrylonitrile in said more highly grafted copolymer being at least 1:6.

12. The process of claim 11 wherein said starch is a thinned starch.

13. The process of claim 11 wherein said starch is a cooked starch.

14. The process of claim 11 wherein said starch is a defatted starch.

15. The process of claim 13 wherein said starch is a thinned starch.

16. The process of claim 11 wherein said ratio of starch to acrylonitrile is within the range of from 1:9 to 1:12.

17. The process of claim 16 wherein approximately one-half of the predetermined amount of acrylonitrile is employed in the first grafting reaction of said starch with acrylonitrile and the remaining one-half portion of the acrylonitrile is employed in the second grafting reaction.

18. A process of preparing a starch acrylonitrile graft copolymer which comprises grafting starch with a portion of a predetermined amount of acrylonitrile in the presence of a free radical initiator, holding said grafting reaction mixture until the reaction is no longer exothermic and the temperature remains substantially constant, increasing the temperature to within the range of from 50° to 70° C. and holding at said temperature range until said grafting reaction is substantially complete; and thereafter, grafting copolymer prepared as above specified with the remaining portion of said predetermined amount of acrylonitrile, in the presence of a free radical initiator, holding said grafting reaction mixture until the reaction is no longer exothermic and the temperature is substantially constant, increasing the temperature within the range of 50° to 70° C and holding until the grafting reaction is substantially completed, the mole ratio of starch to acrylonitrile in the final product being at least 1:6.

* * * * *